United States Patent [19]
Matlock et al.

[11] Patent Number: 5,339,254
[45] Date of Patent: Aug. 16, 1994

[54] INSTRUMENT FOR DETERMINING THE STABILITY OF FAT OR OIL

[75] Inventors: Mark G. Matlock, Mount Zion; Ronald T. Sleeter, Decatur; Tod A. Jebe, Oreana, all of Ill.

[73] Assignee: Archer Daniels Midland Company, Ill.

[21] Appl. No.: 663,576

[22] Filed: Mar. 1, 1991

[51] Int. Cl.⁵ .................. G01N 27/26; G06F 15/20
[52] U.S. Cl. .................. 364/499; 422/98; 436/60
[58] Field of Search ............ 364/499; 422/74, 98, 422/82.02; 436/60, 150; 324/439, 444, 446, 698

[56] References Cited

U.S. PATENT DOCUMENTS

| | | | |
|---|---|---|---|
| 2,752,815 | 8/1952 | Batchelor | 422/74 |
| 4,029,554 | 6/1977 | Ellison | 204/153.1 |
| 4,219,530 | 8/1980 | Kopp et al. | 422/81 |
| 4,686,857 | 8/1987 | Kato | 324/698 |
| 4,764,258 | 8/1988 | Kauffman | 204/153.1 |
| 4,971,523 | 11/1990 | Wacker et al. | 417/63 |
| 5,025,220 | 6/1991 | Colvin et al. | 324/444 |
| 5,071,527 | 12/1991 | Kauffman | 324/439 |
| 5,132,225 | 7/1992 | Dickakian | 436/60 |

Primary Examiner—Ellis B. Ramirez
Attorney, Agent, or Firm—Laff, Whitesel, Conte & Saret

[57] ABSTRACT

A system monitors the stability of fats and oils especially having the capacity of simultaneous analysis of a multitude of samples making it convenient for use to monitor a production plant. A plurality of probes (made from a metal taken from a group consisting of nickel, chromium, rhodium, titanium and stainless steel) have spaced parallel electrodes immersed in a liquid carrier (deionized water) through which an effluent of heated fats or oils is bubbled. A common conductivity meter responds to signals from each of the probes, in turn, for measuring the induction time of the fats or oils samples. The instrument features a power failure recovery system that utilizes a battery-power clock, so that short duration power failures do not cause a loss of data. A long duration power failure does not cause loss of data to the point of failure, however incomplete analyses are stopped.

25 Claims, 6 Drawing Sheets

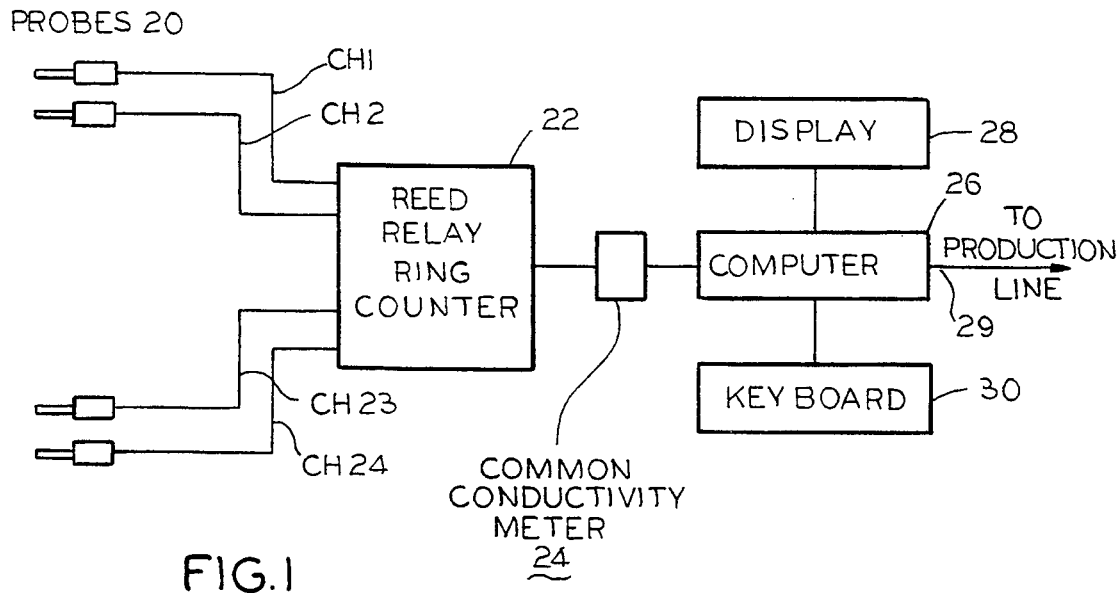
FIG.1
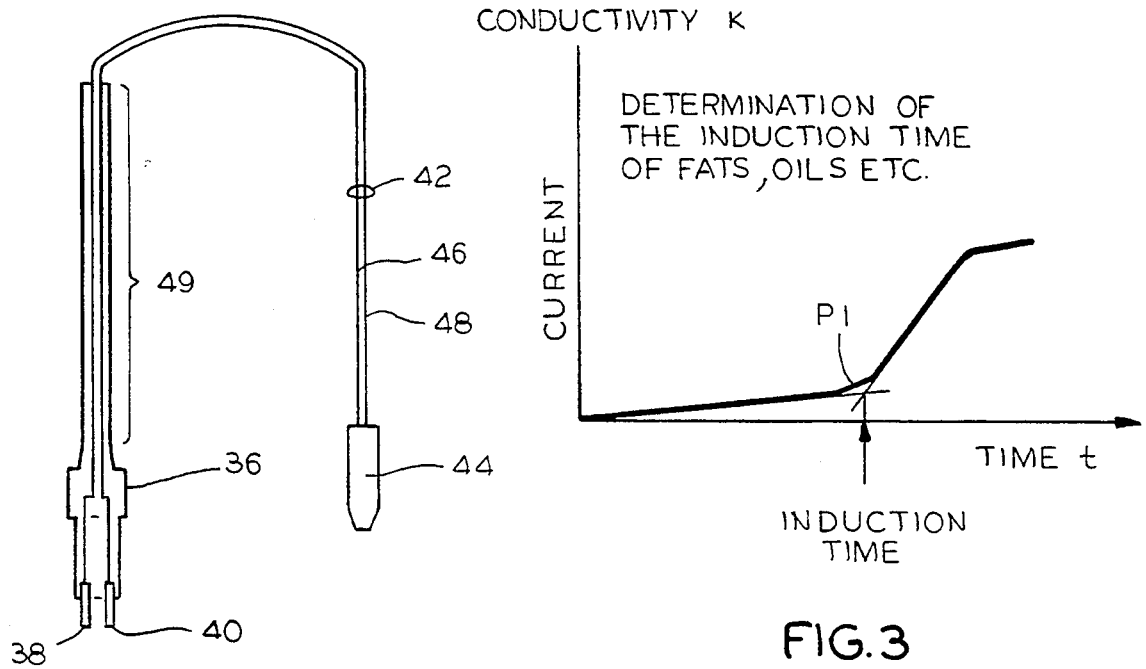
FIG.2
FIG.3

INSTRUMENT FOR DETERMINING THE STABILITY OF FAT OR OIL

This invention relates to instruments for determining the stability of fats and oils particularly a means for measuring conductivity changes in deionized water in which volatile organic acids produced by an oxidation of oils and fats are collected.

According to the American Oil Chemist Society Method Cd 12b-92, all oils and fats have a resistance to oxidation which depends on the degree of saturation, natural or added antioxidants, prooxidants or prior abuse. Oxidation is slow until this resistance is overcome, at which point oxidation accelerates and becomes very rapid. The length of time before this rapid acceleration of oxidation is the measure of the resistance to oxidation and is commonly referred to as the "induction period." The Oil Stability Index (OSI) is defined as the point of maximum change of the rate of oxidation, or mathematically as the maximum of the second derivative of the conductivity with respect to time.

In greater detail, the invention relates primarily to a computerized system for monitoring the quality of auto-oxidizable compounds such as fats and oils. Auto-oxidizable compounds are susceptable to oxidation due to the presence of carbon to carbon double bonds and other labile groups. The inventive instrument measures any inherent resistance to oxidation, as well as the resistance which may occur from a lack of anti-oxidants or may be promoted by pro-oxidants.

In our description we will refer to the analysis of fats and oils products; however, it should be understood that any suitable auto-oxidizable compound could be substituted. While many different products may be mentioned, one exemplary system is the analysis of fats and oils samples produced by a processing plant which produces corn and soy fats and oils. These corn and soy fats and oils become generic ingredients for further use, such as to manufacture margarine, shortenings, salad dressings, baked goods, or the like. Another exemplary system is used to measure the stability of unsaturated polymers such as plastics and elastomers. These materials may be used to make high impact polystyrenes, homo- and copolymers of butadiene, and homo- and copolymers of isoprene.

Heretofore, the manufacturers and users of fats and oils have tended to ignore the analysis of long term oxidative stability. This is because the long and cumbersome AOM test procedure (American Oil Chemists Society official Method CD 12-57) was grossly inaccurate ($\pm 35\%$). Second, this test is dependent upon the titration involving toxic chemicals of several samples after a prolonged aerated heating. The period of heated aeration must be chosen accurately; or, the test will be invalid because the analyst ran out of sample for titration or the endpoint will have been exceeded. Also because the tests are operator dependent and labor intensive, they are both expensive and subject to human error.

Also, the invention is in-part programmed into a computer, which allows the freedom of choosing the method of endpoint determination. The computer collects and stores raw data, which can be mathematically manipulated during or after the analysis to achieve flexibility which may be necessary or desirable to control a production line. Several possibilities include: the maximum of the second derivative, the crossing of a threshold limit of increasing slope, the recalculation of points to average out noise followed by a computation of the endpoint. Regardless of the method chosen for endpoint determination, once the decision is made, the computer program allows the automatic calculation/determination of the induction period of the oxidation of the fat being analyzed commonly called the Oil Stability Index.

Substantially, all fats and oils have a resistance to oxidation. This resistance may result from hydrogenation, added or natural antioxidants, trace levels of prooxidants, or a natural stability due to low amounts of unsaturated fatty acids, etc. The time required to overcome this resistance is called the "induction" period. Once an oil is oxidized past the induction period, the oxidation change occurs very rapidly. The point where oxidation becomes rapid is commonly referred to as "The Oil Stability Index" ("OSI"). References which describe information relative to the techniques described herein for finding the induction period are found in Von H. Pardun and E Kroll in Fette, Seifen und Anstrichmittel 4 366–374 (1972); K. Zurcherin Mitt. Gebiete Lebensm. Hyg. 65, 90–95 (1974); and C. W. van Oosten, C. Poot and A. C. Hensen in Fette, Seifen und Anstrichmittel 4 133–135 (1981). Reference may also be made to U.S. Pat. No. 4,219,530.

One convenient technique for measuring the induction period ("OSI") is to measure the conductivity changes over time in deionized water in which volatile oxidation products derived from the oil are collected. In practice, to make this measurement, air is bubbled through the oil in a heated reaction tube or flask. The bubbling air flow sweeps the volatile oxidation products into another tube or flask containing deionized water and a conductivity probe. The conductance of the oxidation products dissolved in the deionized water is measured over time, with the conductance exactly following the oxidation of the oil.

Previous instruments for measuring the described stability included one or more conductivity meters which were coupled to a strip drive chart recorder. However, this previous type of system is generally limited to making, at most, six simultaneous analyses. This limited capacity is very cumbersome and not normally considered adequate to monitor a modern processing plant.

One instrument of the previous type is sold under the trademark "679 Rancimat", manufactured by Metrohm Ltd., CH-9100 Herisau, Switzerland, and distributed by Brinkmann Instruments, Inc., of Westbury, N.Y. 11590.

Metrohm describes this instrument as being useful "for the determination of the oxidative stability of fats, oils, etc. by an evaluation mode based on the induction time." The instrument can also evaluate the stability of fats and oils according to the conductivity difference which is measured after an expiration of a specified time interval. To perform the oxidative stability test of fats, oils, etc., the sample material is oxidized with air at an elevated temperature. A conductivity measuring cell is used for the continuous detection of the volatile carboxylic acids that are liberated. This Metrohm instrument may test up to six samples at once. A printer strip shows the progress of the determinations. On completion of the test, the instrument provides a printout documenting the results.

Accordingly, an object of this invention is to provide new and improved means for and methods of measuring and recording the stability of fats and oils. In particular, an object is to provide a system for measuring the stability of fats and oils or finished products for up to 24 points in a plant where it is or may be important to make simultaneous analyses of the stability of fats and oils and, additionally, to make tests on end use products such as margarine, shortening, potato chips, crackers, etc. Here, an object is to determine the individual induction time periods or ("OSI") of fats and oils and fat, containing products at each of these points.

Yet another object of the invention is to provide acid resisting probes for measuring the conductance of fats and oils.

In keeping with an aspect of the invention, these and other objects are accomplished by a computer controlled system for sequentially and cyclically measuring each sample. Air sweeps through the area of the heated sample and subsequently into a quantity of deionized water which collects the volatile organic acids. The conductivity of the water is measured to find the induction point referred to as the "Oil Stability Index" ("OSI"). The invention also includes a program for the computer which takes into account the conditions of the system during power failures or warm booting in order to save good data and discard suspect data.

A preferred embodiment of the invention is shown in the attached drawings, wherein:

FIG. 1 is a block diagram of a system employing the invention;

FIG. 2 is a probe used to practice the invention;

FIG. 3 is a graph which shows how conductivity changes over time leading up to a determination of the OSI of fats, oils, etc.;

Figure 4:
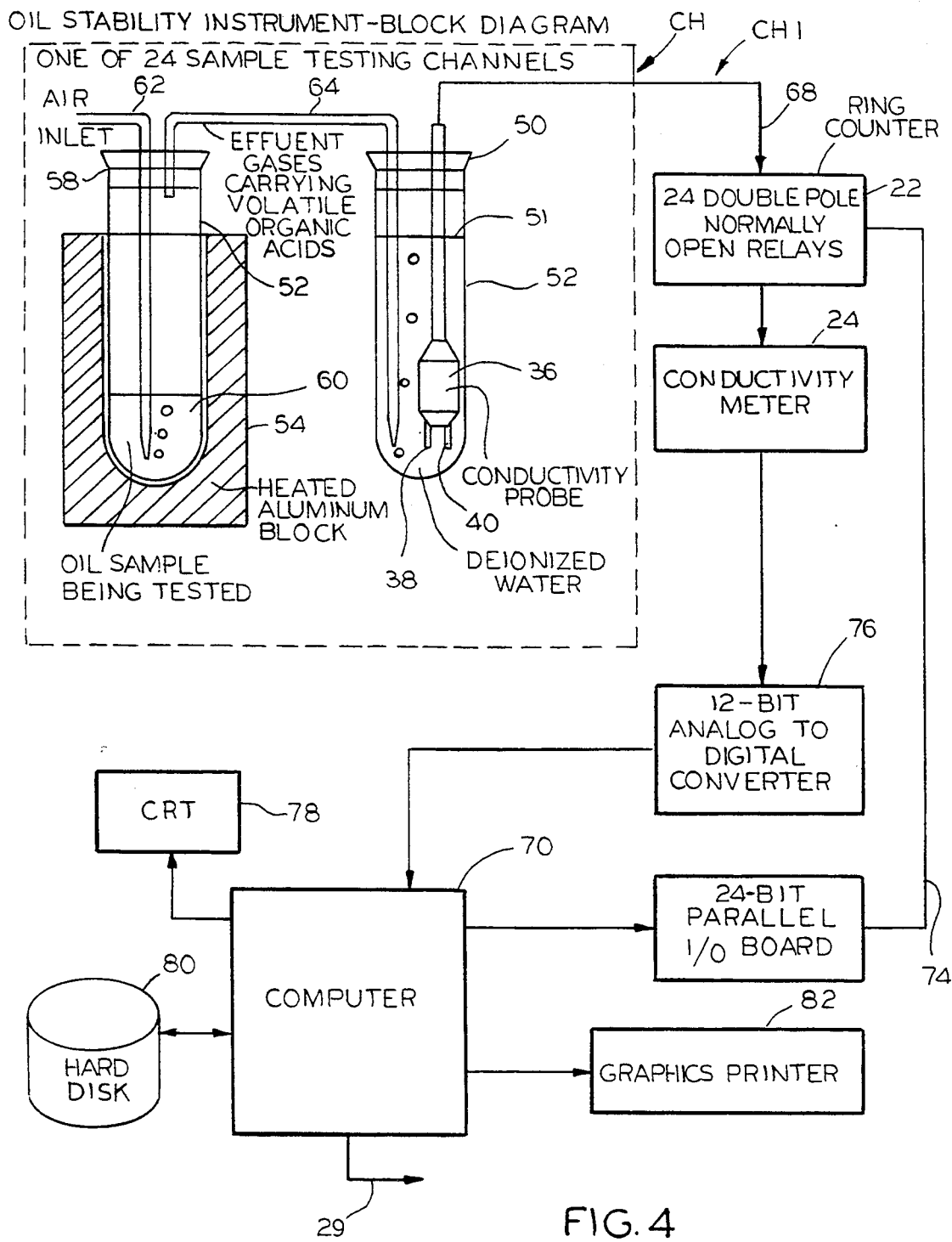
FIG. 4 is a block diagram schematically representing a single channel for finding the inductance ("OSI") of fats and oils.

The invention provides many channels for conducting simultaneous testing with sequential reporting of test results. This large testing capacity is especially important for monitoring and controlling a manufacturing process at many locations.

FIG. 1 shows twenty-four channels of testing capability, by way of example. In greater detail, twenty-four probes 20 are located at any suitable positions in a production line which is manufacturing fats, oils, or the like.

The reed relay ring counter 22 has twenty-four relays which sequentially connect each of the twenty-four channels CH 1 . . . CH 24 to a common meter 24, which may be somewhat similar to the above described Brinkmann instrument, for example.

A relay ring counter is a device which endlessly repeats a cycle of counting steps. For example, a plurality of relays may be coupled to sequentially operate each other in an endless circle. On a first step or clock pulse, relay "1" operates and prepares relay "2". On a second step or clock pulse, relay "1" releases, prepared relay "2" operates and prepares relay "3". If there are twenty-four relays, as here assumed, the twenty-third step or clock pulse releases relay "22" operates relay "23", and prepares relay "24". The twenty-fourth step or clock pulse releases relay "23", operates prepared relay "24", and prepares relay "1". The twenty-fifth step or clock pulse releases relay "24", operates prepared relay "1", and prepares relay "2". Hence, the relays continue to operate, one-at-a-time, and in sequence, as long as operating pulses are received. On each step, an operated relay connects an individually associated channel CH to the common instrument 24.

This common conductivity meter is able to perform up to twenty-four simultaneous analyses. The common conductivity meter 24 feeds the signals produced by the probes 20 to a computer 26 which is programmed to display on screen 28 the test results in any suitable manner. The entire system operation may be controlled from a computer keyboard 30.

FIG. 2 shows the construction of one probe 36 among the probes 20. Two solid metal electrodes 38, 40 are held in a spaced parallel relationship by a suitable block of plastic material. Heretofore, these electrodes have been made of platinum to resist the attack of acids and other chemicals encountered by the probes during normal testing. The electrodes may also be made from materials taken from a group consisting of the following pure or alloyed metals: nickel, chromium, rhodium, titanium and stainless steel. Surprisingly, it has been found that pure nickel is as reliable and as resistant to attack as platinum. These probes are connected to a quick connect connector 44 via individual wires 46, 48, which together form a preferably shielded cable 42.

The preferred probe 36 is constructed with two nickel electrodes 38, 40, each being 18.0 mm long and 3.18 mm in diameter. Each electrode is embedded in plastic at a 8.0 mm depth with 10.0 mm of exposed metal electrode. The exposed electrode ends are rounded and polished. Wire leads are soldered to the electrode ends embedded in plastic and are connected through another 45.0 mm of plastic (19.0 mm in diameter) and a plastic stem 150 mm long and 9.64 mm in diameter 49 to a two wire conductor. The wire 49 is extended for another 41.5 mm length to a female quick disconnect connector 44.

We have found during the course of our investigations that normal commercially available stoppers consisting of neoprene, silicone, SBR, etc., do not have the resistance necessary to withstand an attack by the organic acids produced by this analysis. We have discovered that stoppers made from PVC (polyvinyl chloride) are effective in long term use.

The probe is fitted through a PVC stopper 50 (FIG. 4) and immersed in 50 ml of a suitable liquid carrier 51, such as deionized water, contained in a 24.5×200 mm flask or glass tube. The length of plastic 49 totally protects the probe and provides the rigidity needed for easy handling, setup, and cleaning. When the conductivity is to be determined, the connector 44 of probe 36 is attached to a corresponding male quick connect connector and, in turn, to a conductivity testing circuitry. This probe is fitted with such quick connect capability to provide for easy disassembly and cleaning.

Each channel CH (FIG. 4) of testing equipment begins with a heated aluminum block 54 supporting a flask or glass tube 56 sealed by a PVC stopper 52 containing a sample 60 of oil or fat that is being tested. An air inlet tube 62 passes through stopper 58 and brings air into the flask or tube, the air bubbling up through heated sample 60.

The heat from block 50 vaporizes degradation products from the sample and creates an effluent gas which is carried through tube 64 to this flask or glass tube 52, which is sealed by PVC stopper 50. The flask or tube 52 contains a liquid carrier 51, which is deionized water in this example, through which the effluent received from flask or tube 60 is bubbled. The conductivity of the deionized water 51 changes as a function of organic acids produced by the oxidative degradation of the fat or oil under test dissolve in the deionized water 51, increasing its conductivity over time. Therefore, a current flow through the water 51 and between electrodes 38, 40 of probes 36 causes a signal to be sent over cable 68 to a computer 70 which analyzes the test results. The computer in one exemplary embodiment was an IBM model 30/286.

The counter or ring of reed relays 22 steps endless through a cycle which connects each probe 20 (FIG. 1), one-at-a-time, to the common conductivity meter 24, which gives an output signal in response to the current between the probe electrodes. Each time that the computer 70 accepts a test result from a probe in one channel, it sends a signal over wire 74 to step the reed relay counter 22 one step to select the next channel. After the signal on that channel is read, the relay counter 22 is again stepped on to select the next channel.

A common means beginning with conductivity meter 24 (FIG. 5) provides an analog output signal which represents the magnitude of the current between the probe electrodes 38, 40 and, therefore, the conductivity of water 51. This analog signal is converted into a digital signal by the analog-to-digital converter 76, which may provide a twelve bit output word signal.

These digital signals are fed into computer 70 which analyzes the test results and gives out an indication of the stability of the fats and oils referred to as the Oil Stability Index. As here shown, the resulting output of the computer 70 may be displayed on a cathode ray tube 78, stored on a disk 80, or printed out at 82 in a suitable graphic form. The computer 70 may also send suitable signals over serial communication links 29 to control automatic production equipment in order to hold a factory within an acceptable production range.

The changes in the conductivity of the deionized water 51 (FIG. 4) are shown by the idealized graph of FIG. 3. The conductivity of water 51 increases slowly over time until the induction point P1 is reached. At that time (i.e., at the induction point or "OSI"), the rate of the current flow through water 51 increases abruptly. By detecting the period of time required to reach this induction point P1, the computer is able to indicate the stability of the oil or fat in the sample 60 (FIG. 4).

Figure 5:
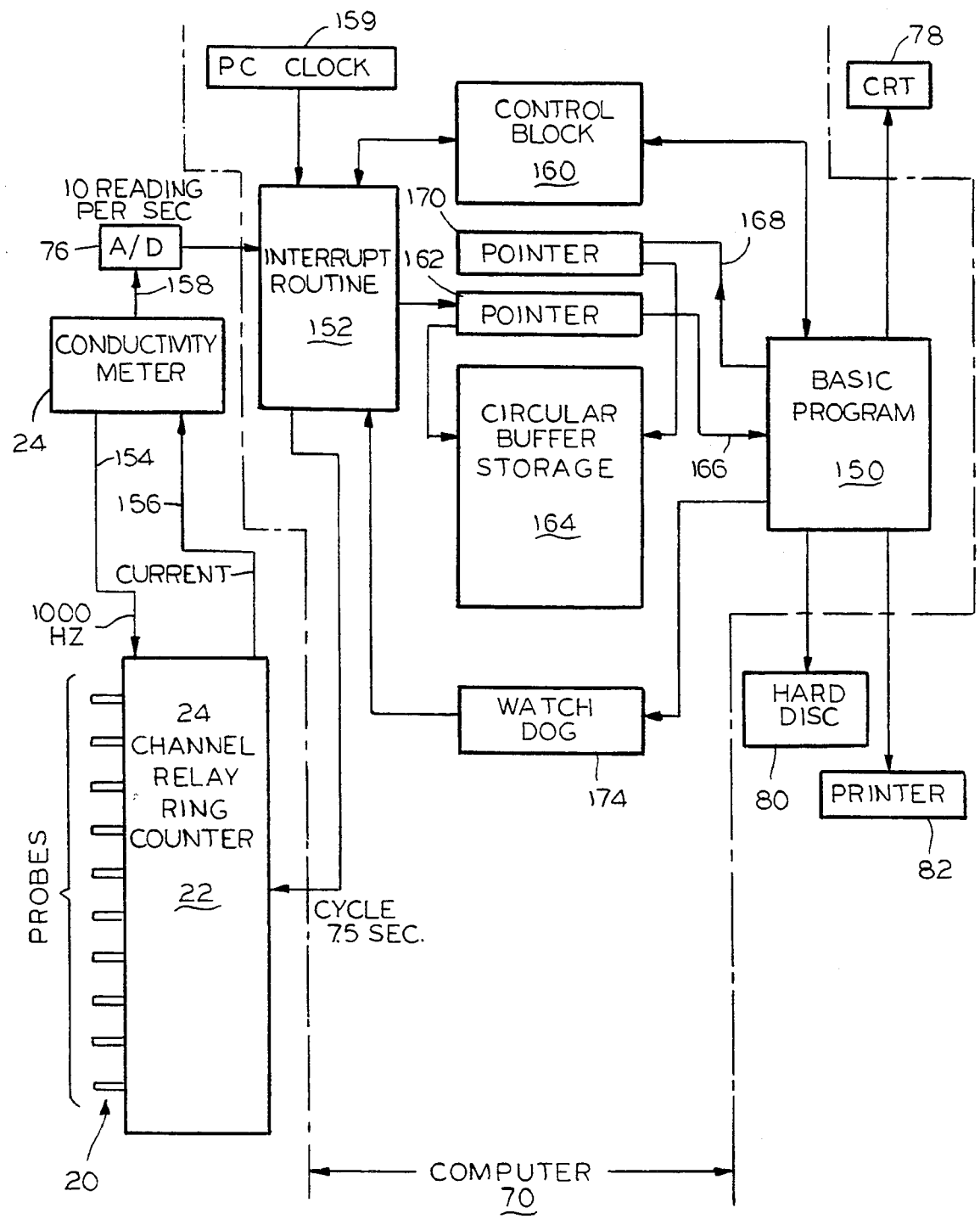
FIG. 5 is a block diagram of the computer of FIG. 4.
Figure 7:
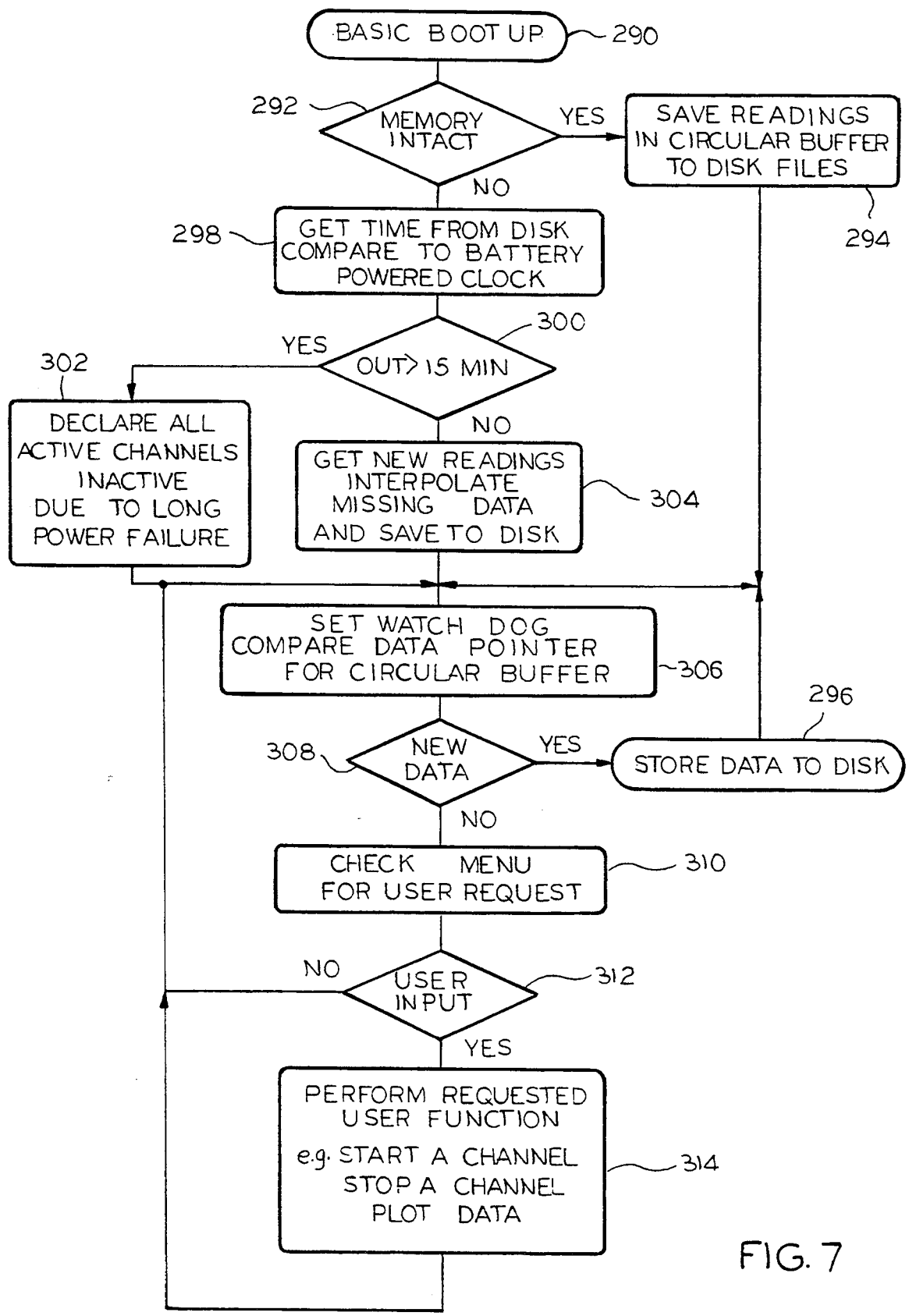
FIG. 7 is a flow chart showing pertinent aspects of a computer which is programmed to practice the invention.
Figure 8:
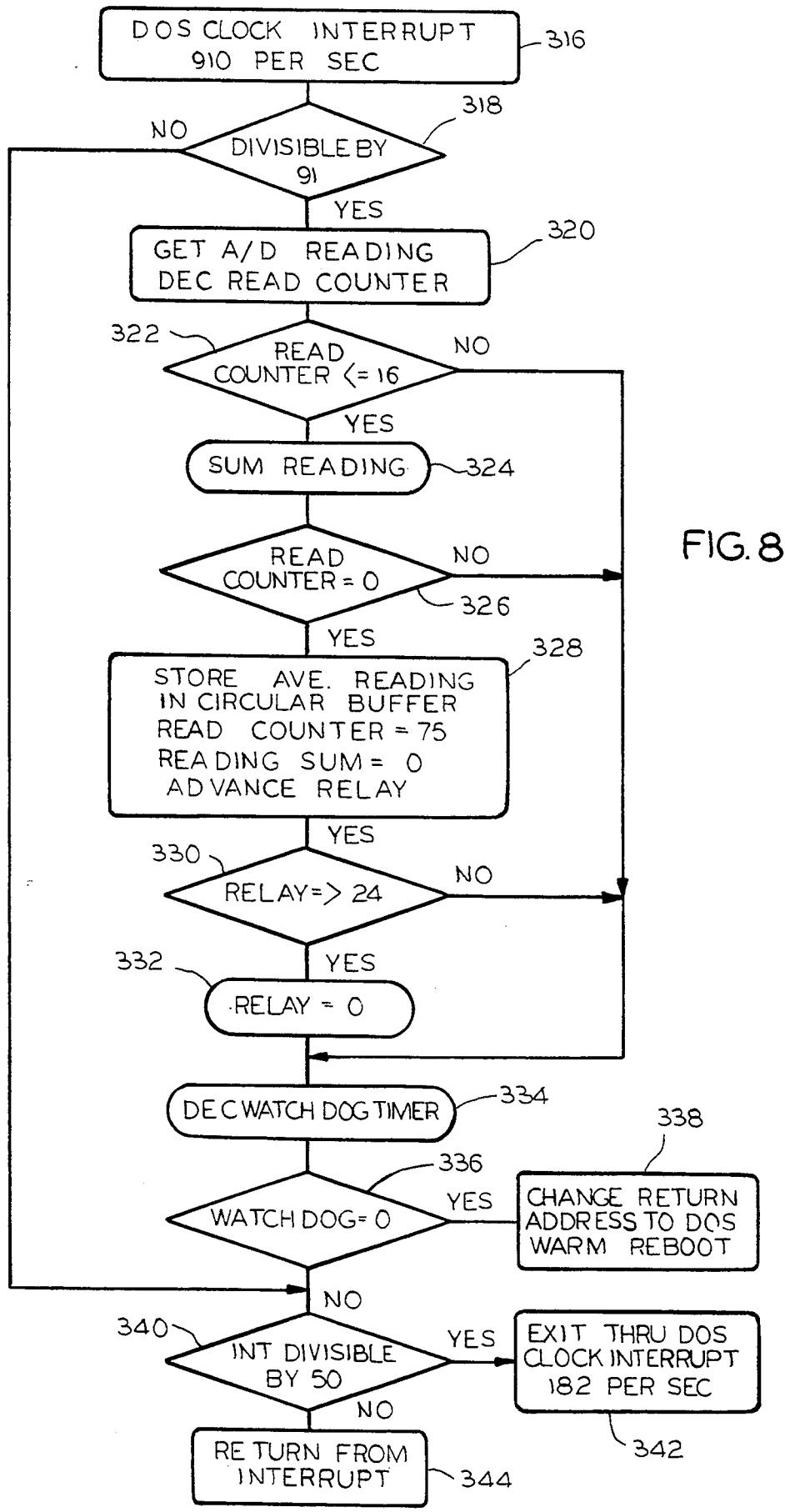
FIG. 8 is a flow chart of an interrupt program for the computer program of FIG. 7 which may be used for controlling the system of FIG. 1.

The equipment which the flow charts of FIGS. 7 and 8 represent are shown in the block diagram of FIG. 5. The same parts are identified by the same reference numerals throughout the drawings. Therefore, the various parts may be oriented relative to each other by comparing the reference numerals. The basic routine of FIG. 7 is carried out in block 150 of FIG. 5. The routine of FIG. 8 is carried out in block 152.

The probes 20 are coupled, one at a time to the common conductivity meter 24 via the relay ring counter 22. At its output 154, common conductivity meter 24 sends a 1000 Hz square wave to a probe 20 as soon as it is connected through ring counter 22. At the meter input 156, the probe returns a current signal which is proportional to the conductivity of the deionized water 51 (FIG. 4), and therefore proportioned to the effluent from the heated sample 60.

The common conductivity meter 24 converts the current signal into a voltage level delivered at meter output 158. This voltage level is converted into a digital signal by the analog-to-digital converter 76 and forwarded to the interrupt routine circuit 152, at a rate of ten readings per second. The interrupt routine circuit 152 is driven at a clock rate determined by the inner workings of a personal computer 70 (FIG. 5).

The interrupt routine circuit 152 and the basic program circuit 150 exchange information over a two way message buffer which is here designated "Control Block" 160. Primarily, the signals in this buffer relate to the inner working of the computer as circuits 150, 152 interact, although some information data is also exchanged via this memory common.

As each item of information data is acquired by the interrupt routine circuit 152, it is forwarded through a pointer circuit 162 to a circular buffer circuit 164.

Perhaps an hour or so of test results may be buffer stored in circuit 164. Since the events are occurring at electronic speeds, the approximately one hour of data storage capacity at 164 is never needed in normal operation. Rather, the large storage capacity provides for retaining data if there is a massive long term failure.

Basically, the pointer circuit 162 is a self-incrementing address register. At any given time, it is resting on an address of a memory location in the circular buffer storage memory 164. As soon as the data of one test is stored in circuit 164, the pointer 162 increments to select the address of the next memory location where the next test data is stored.

The basic program block 150 is a central part of computer 70, which might also be performing many functions other than controlling the tests described herein. The basic program 150 only needs to interrogate buffer storage area 164 before it fills. Therefore, the buffer pointer 162 keeps the basic program circuit 150 informed about the progress of the testing.

The basic program circuit 150 updates circuit 170 to indicate the address of the last data read from buffer storage circuit 164. If the two addresses 166 and 168 do not coincide, the basic program circuit 150 increments pointer 170 and reads the next data stored in buffer 164. This read and increment sequence continues until the same addresses are present in pointers 162 and 170 which means that the basic program circuit 150 has caught up with the buffer 164 and is again operating on a current status of data taking.

After the basic program circuit 150 stores a reading to the hard disk 80, it resets the watch dog timer.

Figure 6:
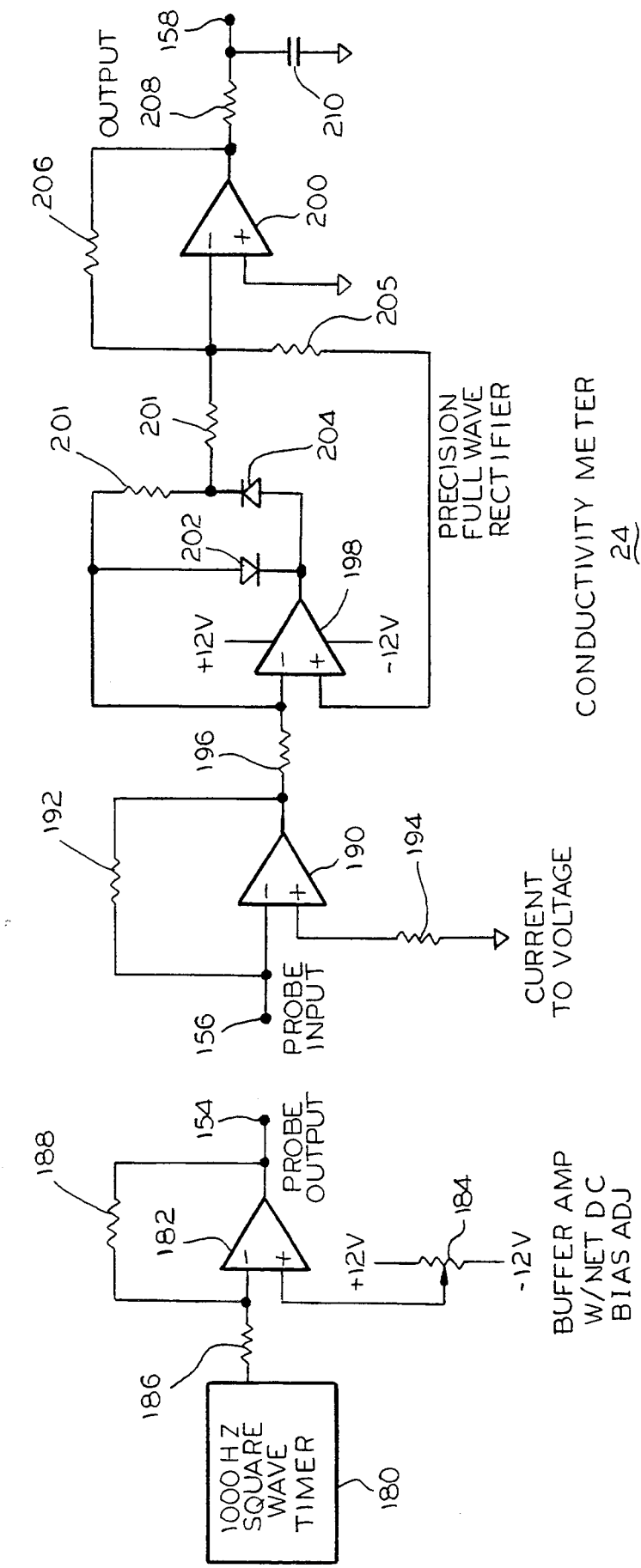
FIG. 6 is a schematic circuit diagram of the conductivity measuring circuit of FIGS. 4 and 5.

The details of the conductivity meter circuit 24 are shown in FIG. 6. The input and output terminals 154, 156, 158 may be compared in FIGS. 5 and 6 to orient the details of FIG. 5 with the details of the block diagram of FIG. 6. The probe uses a shielded cable; therefore, only one wire is required for signalling purposes. The ground return provided via the shielding is the same as the ground potential appearing throughout the system.

The timer 180 produces a 1000 Hz square wave with a 50% duty cycle output. An operational amplifier 182 adjusts the level of the square wave to be 8 V positive and 8 V negative, taken relative to a 0 Volt ground. A voltage divider 184 adjusts the 0 level to center it between these +8 V and −8 V levels. Resistors 186, 188 are selected to make the amplifier 182 behave as a buffer amplifier.

Hence, a 1000 Hz signal is sent to the probe at terminal 154. This signal travels through the deionized water and, at 156, returns to the conductivity meter circuit 24. The operational amplifier 182 adjusts the voltages level of a signal which indicates the current through the deionized water 51 into a voltage level, which also represents the conductivity of the deionized water 51. Resistor 192 provides gain control. Resistor 194 limits current and prevents a short circuit at the input of operational amplifier 190 if the probe electrode terminals are short circuited. Resistor 196 provides coupling.

The operational amplifiers 198, 200 form a full wave rectifier. Resistors 201 provide coupling. The rectification occurs at the diodes 202, 204. Resistor 205 adjusts the voltage level. Since the signal is a square wave and further since there is some capacitance between the probe electrodes, the rectified voltage tends to have voltage spikes followed by a capacitance caused exponential decay at the output of the operational amplifier 200. However, there is a smoothing by the RC filter 206, 208, 210. Thus, a relatively smooth output voltage appears 158.

The outlet voltage at terminal 158 has a level which indicates the conductivity of the deionized water 51 which, in turn, indicates the stability of the fats and oils in sample 60. These are the analog signals which are digitalized at 76.

FIGS. 7 and 8 are flow charts which explain how the computer 70 is programmed. FIG. 7 represents how the normal operation of a computer 70 has been modified to attend to the inventive functions. FIG. 8 represents a sub-routine which is carried out by the computer during discreet intervals in the computer routine.

In greater detail, FIG. 7 begins with a basic computer bootup (start up) 290. This may be the cold start occurring the first time that the computer is turned on. However, a more probable situation is that the computer has been on for an indefinite period of time, perhaps going back hours, days, weeks, or months. Something may have caused the computer to shut down and then restart. For example, the shut down may have been caused by a power failure. Or perhaps a human operator has undertaken an incorrect or forbidden procedure which caused a software impasse and momentarily switched off the computer to reset or warm boot it to break the impasse.

At the time of such switch off, data was being stored in the system. A critical factor is whether or not the system was shut down for a period which was long enough for the aluminum block 54 (FIG. 4) to cool significantly. If it did not cool too much, all previous data is still good and the testing may continue from the point where it left off at the time when the computer shut down. If it did cool too much, the results of any previous and uncompleted tests must be discarded and the test reinitiated.

The basic program bootup occurs at step 290 in FIG. 7. Thereafter, on the first action at step 292, the computer checks its memory banks to determine whether any stored data is intact. If there is apparently valid data in memory, it is stored at step 294 on a suitable memory medium, such as a hard disk at step 296, for example.

If the memory check at 292 indicates that the computer does not include complete data, it compares the time when data was last received from a probe with the current time as indicated by an internal battery-powered clock which was not shut down. This comparison determines whether the interruption was more than fifteen minutes (i.e. a length of time required for aluminum block 54 to cool sufficiently to invalidate the test results).

If the power was off for more than fifteen minutes, a circuit declares at step 300 that all partially completed data is unreliable and, therefore, cancels and discards it at step 302. If power was not shut down for fifteen minutes, at step 304, a circuit requests a completion of the taking of data in order and interpolates the old and new data to supply the missing data. For example, if the previously stored data was "500" and the new data is "1000", the computer supplies a linear change of data beginning at "500" and ending at "1000" as a probable substitute for readings which would have been taken during the power failure.

The circuits which are activated on any step labeled "Watch Dog", in FIGS. 7 and 8 respond to a software supplied format pointer (i.e. from pointer circuit 170) which accompanies each data information reaching the computer. The watch dog is set on any power failure or software hang up which prevents data from coming in.

Essentially, the watch dog timer is a clock driven counter which responds to the absence of a reset operation by program step 306. The interrupt routine (step 316) occurs 910 times per second via the DOS clock interrupt hardware. This interrupt rate can be divided into both an 18.2 hertz rate for this DOS to keep the system time accurate and into a 10 hertz rate for background acquisition. Step 306 resets the watch dog time. It does this by putting a value of "9000" into the watch dog counter. The program step 334 decrements this valve 10 (R) times per second. This will result in a 15 minute (M) time. The watch dog value maybe calculated by the following equation, knowing that (S) is 60 seconds per minute:

$$R \times M \times S \text{ or } 10 \times 15 \times 60 = 9000$$

If the watch dog timer count down from 9000 to 0, then program steps 306, 308 and 296 have not been executed in 15 minutes. This means that the data collected and stored in the circular buffer (164) has not been stored onto the disk by program step 296. This may be due to the user hitting the pause key on the keyboard or a printer not being in a ready status, pausing a screen print operation or the like. When the watch dog counter reaches zero, instead of exiting back to normal program execution, a routine then branches to step 338 which causes the computer to reboot. This will reload the DOS. When the basic program begins execution at program step 290, it will check to determine whether the circular buffer contains valid data in step 292. If it does it will save that data, transferring to disk memory in step 294. If the watch dog time is not zero, the interrupt routine exits back to the basic program in a normal manner. If new data comes in, the circuit checks and then either stores the data taken before shut down (step 296), or checks the menu at step 310 to determine whether the operator has issued new instructions. If the operator has issued new instructions (step 312), they are followed at step 314; then, the watch dog circuit 174 is reset to step 306. If the operator has not issued new instructions, the watch dog program is reset from step 312 directly to step 306.

The software program for conducting the tests is shown by the flow chart of FIG. 8. The DOS clock for interrupt is the most reliable timing device in the computer. Therefore, it is used to control the testing program, as is indicated at step 316. The computer interrupt cycle is a train of pulses cyclically recurring at a rate of 910 per second, in one instance. Therefore, to provide for a desired ten readings per second, the interrupt clock is divided by 91 in step 318.

The particular probe 20 (FIG. 1) which happens to be connected through the reed relay counter 22 to the common conductivity meter 24 is read during step 320. After that test is conducted, the reed relay counter 22 is incremented one step to connect the next probe to the common conductivity meter 24.

The common conductivity meter 24 receives seventy-five readings each time that the counter connects a probe to the instrument. However, all but the last sixteen readings are discarded. The discarded readings interface the timing differences between electronic and relay equipment to avoid errors which might be caused by such things as a relay contact bounce or low pass filter setting. The last sixteen readings are passed to a summing circuit at step 324, which takes an average of them as a valid reading. The average reading is passed on when the sixteen step countdown at step 322 reaches zero.

At step 328, the average test reading is stored in any suitable medium such as a hard disk, for example.

At steps 330, 332, the circuit keeps track of the position of the reed relay counter 22. There are twenty-four channels in this embodiment. Thus, the start of a countdown is noted at step 330 and the completion of the countdown is noted at 332. The program could be modified at step 330 to accommodate any suitable number of changes. In this embodiment, it takes three minutes for all twenty-four relays in the ring counter 22 to operate. Therefore, there is one complete reading from each probe or channel during every three minute period.

Power failures are handled by periodically recording the current time on the disk. After a power failure, the bootup (step 290) of the basic program occurs. Memory would not contain valid data (step 292) so step 298 would compare the current time from a battery powered clock to the time stored on disk. In this way, the duration of the power failure is calculated by the difference between the clock time and the stored time. If this difference is in excess of 15-minutes, the temperature of the heating blocks has cooled enough to cause an error in the test. The channels that were currently testing samples are stopped to prevent invalid results. If the length of the power failure is less than 15-minutes, the number of missing data points are determined. The missing points are linearly interpolated from the last measurement before the power failure to the first point after the power is restored.

In greater detail, twenty-four probes 20 are located at any suitable positions in a production line which is manufacturing products involving fats and oils (corn and soy oil in one example). By way of example, one probe in channel CH 1 might be at an intake point for inserting a starting material into a production system, one probe in channel CH 2 at a heating point, one probe in channel CH 23 at a cooling point, and one probe in channel CH 24 at an output point. The remaining twenty channels may be connected to probes at any other suitable locations. A reed relay ring counter 22 may connect each of the probes to a common instrument 24 which incorporates a multi-tasking data acquisition program.

The data supplied from probes 20 over the twenty-four channels CH 1, CH 2 . . . CH 23, CH 24 are analyzed by meter 24 in real time in order to determine the onset of oxidation and, therefore, the induction time. The induction time required for oxidation to begin is known as the "Oil Stability Index" ("OSI") and is mathematically defined as the maximum in the second derivative of the conductivity, taken with respect to time at a specified temperature.

The conductivity meter 24 determines the stability of fats and oils by measuring conductivity changes in de-ionized water through which volatile organic acids produced by oxidation are collected and measured.

The signals on each channel are measured every three minutes. The meter 24 conducts eight separate measurements and determines the induction time by the use of program where the increase in conductivity must exceed a threshold value for six out of the eight measurements. The threshold value decreases with the length of the analysis time so that the percentage of increase stays proportional. This program has a sensitivity to noise which is much less than the sensitivity of an actual measurement of the second derivative. Also, in order to further reduce noise, for each data point, a large number (such as sixteen) of conductivity measurements are averaged and stored. Binomial smoothing is used to farther reduce noise.

Since a complete analysis may take from four to one hundred hours or more, the instrument also has to be able to tolerate short power failures. This is accomplished by forwarding all data to a disk for storage on a current time base.

At startup after a power failure or other shut down, the computer program compares the time from an internal battery-powered clock to the time stored on the disk with the last data entry. If the time difference is less than 15-minutes, the program determines which channels are actively acquiring data and interpolates the missing data for those channels in response to a comparison of the first new data as it is received and the data that was last stored on disk. The resulting computer generated analysis provides data which is plotted on a screen and dumped to a printer, if desired. During the plotting and printing, the multi-tasking feature of the program continues to gather data.

Those who are skilled in the art will readily perceive how to modify the invention. Therefore, the appended claims are to be construed to cover all equivalent structures which fall within the true scope and spirit of the invention.

The claimed invention is:

1. A system for monitoring the stability of auto-oxidizable compounds, said system comprising a plurality of probes for monitoring numerous fat or oil samples and sending electrical signals indicating the condition of said fat or oil being monitored, common means responsive to said signals from any one of said probes for measuring the oil stability index ("OSI") of said fat or oil being measured by said one probe, means for sequentially coupling individual ones of said probes to said common means for measuring said OSI time responsive to the signals of the coupled probe, and computer means responsive to said signals from said common means for indicating the OSI of samples.

2. The system of claim 1 wherein the tested compounds are fat or oil.

3. The system of claim 1 wherein the tested compounds are auto-oxidizable degradable plastic material.

4. The system of claim 1 and a flask containing a sample of material containing said fat or oil, means for heating said flask to generate effluent gases from said sample, said effluent gases carrying volatile organic acids derived from said fat or oil, means for bubbling said gases through deionized water to change the conductivity of said deionized water as a function of the amount of said organic acid in said gases, each of said probes comprising two electrodes, and means for detecting said conductivity by measuring current flow between said two electrodes while they are immersed in said deionized water with changed conductivity.

5. The system of claim 4 and means for coupling each of said probes via separate and individually associated channels leading from said probes to said sequential coupling means, said sequential coupling means comprising a ring counter having one step for each of said channels, means for coupling each of said channels through individually associated steps of said ring counter to said common means, and means for sequentially and cyclically operating said ring counter through individual ones of said steps endlessly around said ring.

6. The system of claim 1 wherein each of said probes comprise a spaced parallel pair of metal electrodes whereby conductivity may be measured by detecting current flow through a liquid between said electrodes, and said common means is coupled to said electrodes for detecting the length of time required for said current flow through said water to reach an induction point.

7. The system of claim 6 wherein said metal electrode is taken from a group consisting of nickel, chromium, rhodium, titanium and stainless steel and alloys thereof.

8. The system of claim 6 wherein said liquid is deionized water, and means responsive to said probe for measuring the conductivity of said water after volatile oxidation products derived from heating said fat or oil are collected and dissolved in deionized water.

9. The system of claim 6 wherein said liquid is deionized water, and means responsive to said probe for measuring the conductivity of said water after a collection of volatile oxidation products derived from heating said unsaturated polymers such as plastics and elastomers whereby materials may be derived to make high impact polystyrenes, homo- and copolymers of isoprene.

10. The system of claim 6 wherein said probe is fitted with a quick connect connector for easy assembly, disassembly, and cleaning.

11. The system of claim 6 wherein said probe electrodes are made from #200 nickel wire having approximately a 3.18 mm diameter.

12. The system of claim 6 wherein said probe electrodes are made from #416 stainless steel wire having approximately a 3.18 mm diameter.

13. The system of claim 6 wherein said electrodes are made from #404 stainless steel wire 17 having approximately a 3.18 mm diameter.

14. The system of claim 6 and means sealed with a PVC stopper to enclose said electrodes and liquid in a gas tight enclosure.

15. An instrument for measuring the stability of fat or oil or of fat and oil in most end use foods, a few examples of which are: potato chips, pastries, confections, cheeses, cookies, coffee whiteners, creams, icings, etc. either alone of in combination with food products, said instrument comprising means for bubbling air through a heated sample of fat or oil in order to separate more volatile components from said samples, means for sweeping said bubbling air emerging from said heated sample through a deionized water, means for measuring the conductivity of said deionized water as said volatile components are swept through said water, means responsive to said measured conductivity for taking repeated data during a period of time, means for discarding a first plurality of said taken data to allow an initial period for establishing a stability of said instrument, means for averaging a second plurality of said data taken after said allowed period, and means for storing said averaged data.

16. The instrument of claim 15 wherein said instrument is subjected to unpredictable periods of shut down, and means for storing a time signal with each storage of said average data, means response to an end of a shut down period for comparing the time of a last stored time signal with a real time signal to determine the length of said shut down period, means responsive to said comparing means finding that said shut down period was less than a predetermined time period for storing the next available data, and means responsive to said comparing means finding that said shut down period was more than said predetermined time period for discarding any previously taken but unstored data.

17. The instrument of claim 15 and means also responsive to said comparing means finding that the shut down period was less than said predetermined time period for supplying interpolated data readings as a substitute for data which was not taken during said shut down period.

18. The instrument of claim 15 and computer means for controlling and monitoring a production system, and watch dog circuit means in said computer for monitoring an inflow of said data and for indicating when said inflow of data occurs, and means responsible to a less than acceptable stream of said inflowing data for warm booting said computer in an effort to unblock and reset said computer to a program start condition.

19. The instrument of claim 18 wherein there are a plurality of said means for measuring said conductivity of said liquid carrier to monitor said fat or oil at different places in said production line, and means for sequentially connecting said plurality of measuring means one at a time to said means for taking repeated data, each of said measuring means being interrogated by said means for taking data once each cycle of said sequential connecting.

20. The instrument of claim 19 wherein said production system produces said fat or oil, said plurality of measuring means are probes for measuring the stability of said fat or oil at a plurality of different points in said production system.

21. The instrument of claim 20 wherein said computer is a multi-task control means for enabling an adjustment of operations at different places in said production system while being free to perform other of said multi-tasks, and means for buffer storing said data while said computer is performing said other of said multi-tasks, and means responsive to a return of said computer from said other of said multi-tasks for taking in all data stored in said buffer storage means until said computer is updated to a current status of data taking.

22. The instrument of claim 21 wherein there is one of said heated samples associated with each of said different points in said production system, means for sweeping said bubbling air from each of said samples into an individually associated liquid carrier, and said means for measuring said conductivity measures the conductivity in said individually associated liquid carrier.

23. A system for monitoring a stability of fat or oil, said system comprising a computer having an internal source of clock pulses and a battery powered clock for keeping track of time, means responsive to said clock pulses for cyclically reading characteristics of fat or oil at a plurality of different points in said system where the stability of the fat or oil are important to a process, there being one step in said cycle for each of said different points in said system, said means for reading said stability comprising a probe at each of said points, each of said probes having a pair of spaced electrodes immersed in a liquid carrier through which an effluent of heated fats or oils is bubbled, said electrodes being made of a material taken from a group consisting of nickel, chromium, rhodium, titanium and stainless steel, means for taking the stability data many times on each step of said cyclic readings, means for discarding a first plurality of said data taken on each of said steps, means for averaging the remainder of said plurality of said data on each cyclic reading, and means responsive to said averaging for storing said average data as the reading taken on the step.

24. The embodiment of claim 23 wherein said system is subjected to unpredictable periods of shut down, and means for storing a time signal with each storage of said average data, means response to an end of a shut down period for comparing the time of a last stored time signal with a real time signal to determine the length of said shut down period, means responsive to said comparing means finding that said shut down period was less than a predetermined time period for storing the next available data, and means responsive to said comparing means finding that said shut down period was more than said predetermined time period for discarding any previously taken data that was interrupted by said shut down.

25. The system of claim 24 wherein said cyclic reading means comprises a sequential coupling means, means for coupling each of said probes to separate and individually associated channels leading to said sequential coupling means, said sequential coupling means comprising a ring counter having one step individually associated with each of said channels, a common meter for analyzing said stability of said fat or oil, means for sequentially coupling each of said channels during its individually associated steps to supply said data to said common meter, and means for sequentially operating said coupling means to step endlessly around said ring.

* * * * *